US008859589B2

(12) United States Patent
Secrist, III et al.

(10) Patent No.: US 8,859,589 B2
(45) Date of Patent: Oct. 14, 2014

(54) USE OF 4'-THIO-2'-DEOXYNUCLEOSIDES AS ANTI ORTHOPOXVIRUS AGENTS

(75) Inventors: John A. Secrist, III, Birmingham, AL (US); Kamal N. Tiwari, Birmingham, AL (US); Joseph A. Maddry, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 1532 days.

(21) Appl. No.: 12/047,197

(22) Filed: Mar. 12, 2008

(65) Prior Publication Data

US 2012/0136017 A1 May 31, 2012

(51) Int. Cl.
| | |
|---|---|
| *A61K 31/425* | (2006.01) |
| *A01N 43/78* | (2006.01) |
| *A61K 31/513* | (2006.01) |
| *A61K 9/48* | (2006.01) |
| *A61K 9/20* | (2006.01) |

(52) U.S. Cl.

CPC ............. *A61K 31/513* (2013.01); *A61K 9/4858* (2013.01); *A61K 9/4866* (2013.01); *A61K 9/2054* (2013.01)

USPC ........................................... 514/320; 514/274

(58) Field of Classification Search

USPC .......................................................... 514/320

See application file for complete search history.

(56) References Cited

U.S. PATENT DOCUMENTS

| | | | | |
|---|---|---|---|---|
| 5,521,163 A * | 5/1996 | Walker et al. | .................. | 514/50 |
| 5,591,722 A * | 1/1997 | Montgomery et al. | ......... | 514/45 |
| 2005/0053626 A1* | 3/2005 | Harrington | ................ | 424/232.1 |
| 2007/0003608 A1 | 1/2007 | Almond et al. | | |

FOREIGN PATENT DOCUMENTS

EP 0 421 777 B1 4/1991

OTHER PUBLICATIONS

Stewart "Weapons of mass casualties and terrorism response handbook", American Academy of Orthopaedic Surgeons, 2006.*
Neyts et al, Antimicrobial Agents and Chemotherapy, Sep. 2002, p. 2842-2847, vol. 46, No. 9.*
Haraguchi et al, Bioorganic & Medicinal Chemistry 12 (2004) 5309-5316.*

Extended European Search Report issued in related European Application No. 09720026.5 on May 30, 2011.
Rahim et al., "Synthesis and Anti-Herpes Virus Activity of 2'-Deoxy4'-thiopyrimidine Nucleosides"; American Chemical Society 1996; J. Med. Chem., pp. 789-795.
John A. Secrist, III et al.;"Synthesis and Biological Activity of 2'-Deoxy-4'-thio Pyrimidine Nucleosides"; American Chemical Society 1991; J. Med. Chem., 34; pp. 2361-2366.
International Search Report issued in corresponding PCT Application No. PCT/US2009/036869 dated Dec. 28, 2009.
Office Action issued in counterpart Chinese Application No. CN 200980107480.9 dated Nov. 27, 2012.

Kern et al., "Enhanced Inhibition of Orthpoxvirus Replication In Vitro by Alkoxyalkyl Esters of Cidofovir and Cyclic Cidofovir", Antimicrobial Agents and Chemotherapy, Apr. 2012, vol. 46, No. 4, p. 991-995.

Earl R. Kern, "In Vitro Activity of Potential Anti-Poxvirus Agents", Antiviral Research, 57 (2003) p. 35-40.

Verri et al., "Anti-(herpes simplex virus) Activity 4'-tho-2'-deoxyuridines: A Biochemical Investigation for Viral and Cellular Target Enzymes", Biochem. J. (2000) 351, 319-316.

* cited by examiner

*Primary Examiner* — Wu-Cheng Winston Shen
*Assistant Examiner* — Jean Cornet
(74) *Attorney, Agent, or Firm* — Novak Druce Connolly Bove + Quigg LLP

(57) ABSTRACT

Compound represented by the formulae:

wherein each R individually is H or aliphatic acyl or aromatic acyl group; X is selected from the group consisting of hydrogen, fluoro, chloro, bromo, iodo, alkoxy, alkyl, haloalkyl, alkenyl, haloalkenyl, alkynyl, amino, monoalkylamino, dialkylamino, cyano, aryl and nitro; pharmaceutically acceptable salts thereof, prodrugs thereof and mixtures thereof are used as inhibitors of orthopoxviruses and for treating patients suffering from an orthopoxvirus infection such as, but not limited to, smallpox, cowpox, monkeypox and camelpox.

7 Claims, No Drawings

USE OF 4'-THIO-2'-DEOXYNUCLEOSIDES AS ANTI ORTHOPOXVIRUS AGENTS

FEDERALLY SPONSORED RESEARCH AND DEVELOPMENT

This invention was supported by Grant AI057175 from National institute of health and the US Government has certain rights in the invention.

TECHNICAL FIELD

The present disclosure relates to certain pyrimidine nucleosides that are useful as inhibitors of orthopoxviruses including but not limited to smallpox. The present disclosure relates to methods of using the compounds for treating patients suffering, from diseases caused by orthopoxvirus infections.

BACKGROUND

Orthopoxviruses include variola, cowpox, monkeypox and camelpox. Within the orthopoxvirus family variola virus, the causative agent of smallpox, is very transmissible by the air from person to person. All over the world a major population is highly susceptible to this virus. Smallpox has high morbidity and about 30% mortality. Since this disease has not been in occurrence for at least two decades, the diagnosis would be very difficult especially in a major outbreak. Currently, there is a vaccine which can be effective in the first few days of outbreak, but there is no approved drug to treat smallpox. In a post 911 world, we are living in a dangerous phase of terrorism. In a scenario of a possible bioterrorist attack with a poxvirus and with the complexities of the infection, significant attention has been given to the development of effective anti orthopoxvirus agents other than vaccines.

SUMMARY OF DISCLOSURE

In particular, the present disclosure relates to a method for inhibiting orthopoxvirus in a patient by administering to the patient at least one compound represented by the formulae:

wherein each R individually is selected from the group consisting of H, aliphatic acyl and aromatic acyl group; and X is selected from the group consisting of hydrogen, halo, alkoxy, alkyl, haloalkyl, alkenyl, haloalkenyl, alkynyl, amino, monoalkylamino, dialkylamino, cyano, aryl and nitro;
a pharmaceutically acceptable salt thereof, a prodrug thereof and mixtures thereof; in an amount effective for inhibiting poxvirus.

A still further aspect of the present disclosure relates to a method for treating a patient suffering from an orthopoxvirus infection which comprises administering to said patient an effective amount of at least one of the above disclosed compounds.

Still other objects and advantages of the present disclosure will become readily apparent by those skilled in the art from the following detailed description, wherein it is shown and described preferred embodiments, simply by way of illustration of the best mode contemplated. As will be realized the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES

In particular, the present disclosure relates to use of compounds represented by the following formulae:

wherein each R individually is selected from the group consisting of H, aliphatic acyl and aromatic acyl group; and X is selected, from the group consisting of hydrogen, halo, alkoxy, alkyl, haloalkyl, alkenyl, haloalkenyl, alkynyl, amino, monoalkylamino, dialkylamino, cyano, aryl and nitro;
a pharmaceutically acceptable salt thereof, a prodrug thereof and mixtures thereof.

Listed below are definitions of various terms used to describe this invention. These definitions apply to the terms as they are used throughout this specification, unless otherwise limited in specific instances, either individually or as part of a larger group.

Typical aliphatic acyl groups contain 1 to 6 carbon atoms and include formyl, acetyl and propionyl.

Typical aromatic acyl groups include unsubstituted and alkyl substituted aromatic groups containing 7 to 10 carbon atoms in the aromatic ring. When substituted the alkyl group typically contains 1-6 carbon atoms. Typical aromatic acyl groups include benzoyl and para-toluoyl.

The term "alkyl" refers to straight or branched chain unsubstituted hydrocarbon groups of typically 1 to 22 carbon atoms, more typically 1 to 8 carbon atoms, and even more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

Suitable haloalkyl groups typically contain 1-6 carbon atoms and can be straight or branched chain and include Cl, Br, F or I, substituted alkyl groups including the above specifically disclosed alkyl groups.

Suitable alkenyl groups typically contain 2-6 carbon atoms and include ethenyl and propenyl.

Suitable haloalkenyl groups typically contain 1-6 carbon atoms and include Cl, Br F or I, substituted alkenyl groups including the above specifically disclosed alkenyl groups.

Suitable alkynyl groups typically contain 1-6 carbon atoms and include ethynyl and propynyl.

Suitable monoalkylamino groups for X contain 1-6 carbon atoms and include monomethylamino; monoethylamino, mono-isopropylamino, mono-n-propylamino, mono-isobutyl-amino, mono-n-butylamino and mono-n-hexylamino. The alkyl moiety can be straight or branched chain.

Suitable dialkylamino groups contain 1-6 carbon atoms in each alkyl group. The alkyl groups can be the same or different and can be straight or branched chain. Examples of some suitable groups are dimethylamino, diethylamino, ethylmethylamino, dipropylamino, dibutylamino, dipentylamino, dihexylamino, methylpentylamino, ethylpropylamino and ethylhexylamino.

Examples of halo groups are Cl, F, Br and I.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted such as with a halo or alkyl group.

It is of course understood that the compounds of the present disclosure relate to all optical isomers and stereo-isomers at the various possible atoms of the molecule, unless specified otherwise.

The compounds according to this disclosure may form prodrugs at hydroxyl or amino functionalities using alkoxy, amino acids, etc. groups as the prodrug forming moieties. For instance, the hydroxymethyl position may form mono-, di- or triphosphates and again these phosphates can form prodrugs. For example, see Meier, CycloSal Phosphates as Chemical Trojan Horses for Intracellular Nucleotide Glycosyl—Monophosphate Delivery—Chemistry Meets Biology, European Journal of Organic Chemistry (2006), (5), 1081-1102, Wiley-VCH Verlag GmbH & Co. KGaA, Chemical Abstracts 144: 391234; Drontle et al, Designing a Pronucleotide Stratagem: Lessons from Amino Acid Phosphoramidates of Anticancer and Antiviral Pyrimidines, Mini-Reviews in Medicinal Chemistry (2004), 4(4), 409-419, Bentham Science Publishers Ltd., Chemical Abstracts 141:230392; Cahard et al, Aryloxy Phosphoramidate Triesters as Protides, Mini-Reviews in Medicinal Chemistry (2004), 4(4), 371-381, Bentham Science Publishers Ltd., Chemical Abstracts, 141:218130 and Meier, CycloSal-Pronucleotides-Design of the Concept, Chemistry, and Antiviral activity, Advances in Antiviral Drug Design (2004), 4, 147-213, Elsevier. B.V, Chemical Abstracts 141:133365.

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

Pharmaceutically acceptable salts of the compounds of the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

Compound Synthesis

Compounds of the present disclosure can be prepared according to methods described in Secrist III at al. "Synthesis and Biological Activity of 2'-Deoxy-4'-thio Pyrimidine Nucleotides", J. Med. Chem. 1991, 34, 2361 2366; Rahim, "Synthesis and Anti-Herpes Virus Activity of 2'-Deoxy-4'-thiopyrimidine Nucleotides", J. Med. Chem. 1996, 39, 789-795, U.S. Pat. No. 5,591,722 to Montgomery et al. and assigned to Southern Research Institute, the assignee of this application and European Patent 0 421 777 B1 to Walker et al; entire disclosures of which are incorporated herein by reference. By way of example, the following scheme using 5-iodo-4'-thio-2'-deoxyuridine is presented to further facilitate an understanding of this disclosure.

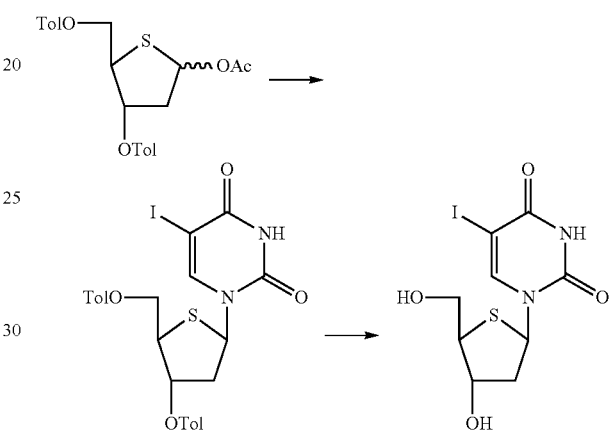

The present disclosure is concerned with inhibiting orthopoxvirus and with treating a patient suffering from a orhtopoxvirus infection. An example of orthopoxvirus is variola virus, which causes smallpox. Examples of orthopoxvirus infections are smallpox, cowpox, monkeypox and camelpox.

The following non-limiting examples are presented to further illustrate the present disclosure.

EXAMPLE

In cell culture, 5-iodo-4'-thio-2'-deoxyuridine was effective at concentrations less than 1.0 μM against wild-type VV (Vaccinia Virus) and (CV Cowpox Virus). In addition, it retained its antiviral activity against several mutant strains of VV including thymidine kinase deficient and dUTPase deficient mutants, as well as, cidofovir-resistant and ST-246 resistant strains. In vitro cytotoxicity was measured by neutral red uptake and CellTiter-Glo® cell viability assays and indicated a cell cytotoxic ($CC_{50}$) value of greater than 100 μM for this compound using either method.

To determine if this compound had activity in vivo, mice were lethally infected intranasally with either VV or CV. In the initial experiments, 5-iodo-4'-thio-2'-deoxyuridine was administered i.p. twice daily at 5, 15 or 50 mg/kg beginning 24 hr post VV infection and continued for 5 days. Treatment with 5-iodo-4'-thio-2'-deoxyuridine completely protected VV-infected mice from mortality at all doses (P<0.001). In a second experiment, 5-iodo-4'-thio-2'-deoxyuridine was administered i.p. twice daily at 1.5, 5 or 15 mg/kg beginning 24 hr after infection with CV and continued for 5 days and again treatment resulted in complete protection from mortality at all doses (P<0.001).

To determine if 5-iodo-4'-thio-2'-deoxyuridine had activity when administered orally, the compound was given by oral, gavage twice daily at 5, 15 and 50 mg/kg. Again, a significant reduction in mortality at all doses (P<0.001) was observed.

The above results indicate that. 5-iodo-4'-thio-2'-deoxyuridine has promise for treatment of adverse reactions to smallpox vaccinations, monkeypox or smallpox disease.

The following Table shows the effect of twice daily oral treatment with 5-iodo-4'-thio-2'-deoxyuridine on the morality of Balb/C mice inoculated intranassally with cowpox Virus-BR.

Effect of Twice Daily Oral Treatment with 5-iodo-4'-thio-2'-deoxyuridine on the Mortality of BALB/c Mice Inoculated Intranasally with Cowpox Virus-BR

| Treatment[a] | Mortality Number | Mortality Percent | P-value | MDD ± STDEV[b] | P-value |
|---|---|---|---|---|---|
| Placebo + 24 hr | | | | | |
| 10% DMSO in 0.4% CMC | 15/15 | 100 | — | 9.8 ± 3.1 | — |
| Cidofovir + 24 hr | | | | | |
| 15 mg/kg | 0/15 | 0 | <0.001 | — | — |
| 5-iodo-4'-thio-2'-deoxyuridine + 24 hr | | | | | |
| 15 mg/kg | 0/15 | 0 | <0.001 | — | — |
| 5 mg/kg | 0/15 | 0 | <0.001 | — | — |
| 1.5 mg/kg | 0/13 | 0 | <0.001 | — | — |
| Placebo + 48 hr | | | | | |
| 10% DMSO in 0.4% CMC | 15/15 | 100 | — | 8.7 ± 1.9 | — |
| Cidofovir + 48 hr | | | | | |
| 15 mg/kg | 0/15 | 0 | <0.001 | — | — |
| 5-iodo-4'-thio-2'-deoxyuridine + 48 hr | | | | | |
| 15 mg/kg | 1/15 | 7 | <0.001 | 18.0 | 0.09 |
| 5 mg/kg | 2/15 | 13 | <0.001 | 16.0 ± 2.8 | <0.05 |
| 1.5 mg/kg | 0/15 | 0 | <0.001 | — | — |
| Placebo + 72 hr | | | | | |
| 10% DMSO in 0.4% CMC | 14/15 | 93 | — | 11.9 ± 2.2 | — |
| Cidofovir + 72 hr | | | | | |
| 15 mg/kg | 0/14 | 0 | <0.001 | — | — |
| 5-iodo-4'-thio-2'-deoxyuridine + 72 hr | | | | | |
| 15 mg/kg | 1/15 | 7 | <0.001 | 14.0 | NA |
| 5 mg/kg | 0/15 | 0 | <0.001 | — | — |
| 1.5 mg/kg | 2/15 | 13 | <0.001 | 14.0 ± 5.7 | NA |

[a]5-iodo-4'-thio-2'-deoxyuridine was suspended in 10% DMSO in 0.4% CMC and given p.o. in 0.2 ml doses. Cidofovir was prepared in sterile saline and given i.p. in 0.1 ml doses. Animals were treated twice daily for five days, except for Cidofovir which was dosed once daily, beginning 24, 48, and 72 hours after viral inoculation.

[b]MDD = Mean Day of Death. STDEV = Standard Deviation.

[c]NS = Not significant when compared to the placebo control.

Formulations

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents such as interferon (IFN), interferon α-2a, interferon α-2b, consensus interferon (CIFN), ribavirin, amantadine, remantadine, interleukine-12, ursodeoxycholic acid (UDCA), and glycyrrhizin or other agents contemplated for the treatment of orthopoxvirus infections.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The, active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing. 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A method for treating a patient suffering from an orthopoxvirus infection which comprises administering to said patient an effective amount of a compound represented by the formula:

wherein X is iodo and R is H; a pharmaceutically acceptable salt thereof or a mixture thereof.

2. The method of claim 1 wherein said patient is suffering from smallpox, cowpox, monkeypox or camelpox.

3. The method of claim 1 wherein said patient is suffering from smallpox.

4. The method of claim 1 wherein said patient is suffixing from monkeypox.

5. The method of claim 1 wherein said wherein said patient is suffering from cowpox.

6. The method of claim 1 wherein said wherein said patient is suffering from camelpox.

7. The method of claim 1 which further comprises administering a therapeutic agent in addition to said at least one compound.

* * * * *